US012633417B2

(12) United States Patent
Rantalainen et al.

(10) Patent No.: US 12,633,417 B2
(45) Date of Patent: May 19, 2026

(54) SYSTEM FOR CANCER PROGRESSION RISK DETERMINATION

(71) Applicant: Stratipath AB, Solna (SE)

(72) Inventors: Mattias Rantalainen, Solna (SE); Yinxi Wang, Solna (SE); Johan Hartman, Bromma (SE)

(73) Assignee: Stratipath, Solna (SE)

( * ) Notice: Subject to any disclaimer, the term of this patent is extended or adjusted under 35 U.S.C. 154(b) by 0 days.

(21) Appl. No.: 18/693,094

(22) PCT Filed: Sep. 27, 2022

(86) PCT No.: PCT/EP2022/076862
§ 371 (c)(1),
(2) Date: Mar. 18, 2024

(87) PCT Pub. No.: WO2023/052367
PCT Pub. Date: Apr. 6, 2023

(65) Prior Publication Data
US 2024/0331874 A1 Oct. 3, 2024

(30) Foreign Application Priority Data
Sep. 28, 2021 (SE) .................................... 2151185-2

(51) Int. Cl.
*G16H 50/30* (2018.01)
*A61B 5/00* (2006.01)
(Continued)

(52) U.S. Cl.
CPC .............. *G16H 50/30* (2018.01); *G06N 3/02* (2013.01); *G06N 3/092* (2023.01); *G06V 10/82* (2022.01);
(Continued)

(58) Field of Classification Search
CPC ........ G16H 50/30; G16H 30/40; G16H 50/70; G16H 50/20; G06N 3/02; G06N 3/092;
(Continued)

(56) References Cited

U.S. PATENT DOCUMENTS

| | | | |
|---|---|---|---|
| 10,810,736 B2 | 10/2020 | Fuchs et al. | |
| 2017/0032090 A1* | 2/2017 | Kamen | ................... G06N 20/00 |

(Continued)

FOREIGN PATENT DOCUMENTS

| | | | |
|---|---|---|---|
| WO | WO-2014144657 A2 * | 9/2014 | ........... C12Q 1/6886 |
| WO | 2018165103 A1 | 9/2018 | |

(Continued)

OTHER PUBLICATIONS

Youden, W.J. "Index for rating diagnostic tests." Cancer 3.1 (1950): 32-35).

(Continued)

*Primary Examiner* — Hajime Rojas
(74) *Attorney, Agent, or Firm* — Noréns Patentbyrå AB

(57) ABSTRACT
There is provided a method comprising determining cancer progression risk for a cancer patient by providing a digital image to a trained neural network and allowing the trained neural network to predict cancer progression risk for the patient based on that image, where the neural network has been trained by receiving a training dataset comprising digital images of histology samples from cancer patients where each histology sample is associated in the dataset with one histology grade score selected from a set comprising three histology grade scores: a first histology grade score indicating low risk for progression of the cancer disease, a second histology grade score indicating intermediate risk for progression of the cancer disease and a third histology grade score indicating high risk for progression of the cancer disease,
(Continued)

using the digital images of histology samples associated with the first and third histology grade scores, while ignoring digital images associated with the second histology grade score, to train a neural network for determining the cancer progression risk for a patient.

12 Claims, 9 Drawing Sheets

(51) Int. Cl.

| | |
|---|---|
| *G06N 3/02* | (2006.01) |
| *G06N 3/092* | (2023.01) |
| *G06V 10/82* | (2022.01) |
| *G16H 30/40* | (2018.01) |
| *G16H 50/20* | (2018.01) |
| *G16H 50/70* | (2018.01) |

(52) U.S. Cl.
CPC ............. *G16H 30/40* (2018.01); *G16H 50/70* (2018.01); *A61B 5/4842* (2013.01); *G06T 2207/20081* (2013.01); *G06T 2207/30068* (2013.01); *G06T 2207/30096* (2013.01); *G16H 50/20* (2018.01)

(58) Field of Classification Search
CPC .................. G06V 10/82; A61B 5/4842; G06T 2207/20081; G06T 2207/30068; G06T 2207/30096
See application file for complete search history.

(56) References Cited

U.S. PATENT DOCUMENTS

| | | | |
|---|---|---|---|
| 2017/0091937 | A1 | 3/2017 | Barnes et al. |
| 2017/0116387 | A1 | 4/2017 | El-Zehiry et al. |
| 2017/0270666 | A1 | 9/2017 | Barnes et al. |
| 2019/0295252 | A1 | 9/2019 | Fuchs et al. |
| 2021/0233251 | A1 | 7/2021 | Rothrock et al. |
| 2022/0148178 | A1* | 5/2022 | Glas ....................... G16B 40/00 |

FOREIGN PATENT DOCUMENTS

| | | |
|---|---|---|
| WO | 2020014477 A1 | 1/2020 |
| WO | 2020261179 A1 | 12/2020 |
| WO | 2021016131 A1 | 1/2021 |
| WO | 2021141742 A1 | 7/2021 |
| WO | 2021198279 A1 | 10/2021 |

OTHER PUBLICATIONS

Bauer, Markus et al., Histological grading of the prostate carcinoma using deep learning: an unsupervised approach. Progress in biomedical optics and imaging Spie—Intl. society for optical engineering. vol 11603. Feb. 15, 2021.

Husein Perez et al., Improving the accuracy of convolutional neural networks by identifying and removing outliner images in datasets using t-SNE, Mathematics vol. 8, No. 5, Apr. 7, 2020, p. 662.

Russakovsky, Olga et al. "Imagenet large scale visual recognition challenge." International journal of computer vision 115.3 (2015): 211-252.

Szegedy, Christian, et al. "Rethinking the inception architecture for computer vision." Proceedings of the IEEE conference on computer vision and pattern recognition. 2016.

Wang, Y. et al., Predicting molecular phenotypes from histopathology images . . . Cancer Research c. 81, No. 19, p. 5115-5126. Jan. 1, 2021.

\* cited by examiner

1

Training Dataset ~2

Neural network ~3

Image selection software ~15

Image processing module ~4

Background removal module ~8

Tiling module ~9

Blur detection module ~10

Filtering module ~11

Color normalization module ~12

Tissue identification module ~13

1

100   BACKGROUND REMOVAL

101   TILING

102   BLUR DETECTION

103   COLOR NORMALIZATION

104   IDENTIFIATION OF CANCER TISSUE

105   FILTERING

RECEIVE IMAGE WITH HISTOLOGY GRADE SCORE 200

DIVIDE IMAGE INTO SUB PARTS 201

ASSIGN HISTOLOGY GRADE SCORE TO ALL SUB PARTS 202

USE SUB PARTS TO TRAIN NEURAL NETWORK 203

300 RECEVIE TRAINING DATA SET

301 USE IMAGES OF TUMORS WITH FIRST AND THIRD GRADE SCORES WHILE IGNORING IMAGES WITH SECOND GRADE SCORE TO TRAIN NEURAL NETWORK

302 USE TRAINED NEURAL NETWORK TO DETERMINE PROGRESSION RISK

22

23a

23b

23c

23b

23a

23c

400 RECEIVE IMAGE

401 DIVIDE IMAGE INTO SUB PARTS

402 DETERMINE RISK FOR EACH SUB PART

403 DETERMINE GLOBAL RISK

SYSTEM FOR CANCER PROGRESSION RISK DETERMINATION

FIELD OF THE INVENTION

This invention relates to cancer diagnostics using a data model, in particular machine learning in relation to histology samples.

BACKGROUND

Cancer progression or recurrence is when a cancer reoccurs after surgery or other treatment. The risk for cancer progression for an individual patient is often used to select follow-on treatment for the patient after surgery of a primary tumor. The treatment is selected based on the risk for cancer progression, where a more aggressive treatment, such as chemotherapy, is used for patients with higher risk and a more conservative treatment is used for patients with low risk. Errors in determining the classification results in risks for under- or over treatment.

Histologic grade assessment in cancer, in particular risk for breast cancer progression, is currently conducted manually by pathologist. This is associated with a significant inter-observer variability, leading to errors in selection of follow-on treatment.

The most broadly adopted grading classification system for breast cancer is the Nottingham grading system modified by Elston and Ellis from the Bloom-Richardson grading system. These grading systems are used to grade a histologic sample in one of three groups using scores. For the Nottingham grading system, the grades are NHG 1, NHG 2 and NHG 3, where NHG 1 is associated with a low risk for progression, NHG2 is associated with an intermediate risk for progression and NHG 3 is associated with a high risk of progression.

The NHG 2 group accounts for approximately half of the patient population and exhibits a large variability with regard to morphological patterns and survival outcomes compared to NHG grades 1 and 3. The heterogeneity of the NHG 2 group poses challenges for deciding optimal treatment for individual patients.

There is a need for an improved method for histologic grade assessment in cancer. In particular there is need for an improved method for classifying patient that belong to the intermediate cancer progression risk group (for example NHG 2).

SUMMARY OF INVENTION

In a first aspect of the invention there is provided a method comprising determining cancer progression risk for a breast cancer patient by providing a digital image of a histological sample from the patient to a trained neural network and allowing the trained neural network to predict cancer progression risk for the patient based on that image, where the neural network has been trained by a) receiving a training dataset comprising digital images of histology samples from breast cancer patients where each histology sample is associated in the dataset with one histology grade score selected from a set comprising three histology grade scores: a first histology grade score indicating low risk for progression of the cancer disease, a second histology grade score indicating intermediate risk for progression of the cancer disease and a third histology grade score indicating high risk for progression of the cancer disease, b) using the digital images of histology samples associated with the first and third histology grade scores, while ignoring digital images associated with the second histology grade score, to train a neural network for determining the cancer progression risk for a patient.

It is surprising that very good results can be obtained by leaving out the second grade group from the training dataset.

In one embodiment, step a) comprises

I. dividing the digital image associated with the histology grade score in the training dataset into a plurality of image sub areas and storing each image sub area as a separate digital image, II. assigning, in the training dataset, the histology grade score associated with the image to every digital image of a sub area, III. using some or all images of the sub areas as classified in ii. to train the neural network in step b).

Dividing the images into sub parts (tiling) has the advantage of simplifying processing by system 1. Smaller images are more easily handled by the system 1.

It is surprising that very good results can be obtained by assigning the same the same histology grade score to each of the tiles.

In one embodiment at least two sub areas of at least one image depicts tissue that would have been graded differently from each other by a pathologist only looking at that sub image.

In one embodiment cancer progression risk for the patient is determined by

A. dividing the provided digital image into a plurality of image sub areas,

B. determine cancer progression risk for each of the sub areas, resulting in a plurality of cancer progression risk values, C. determining a global cancer progression risk by using the plurality of risk values.

In one embodiment the cancer progression risk score determination is carried out for a patient who has previously been considered to have an intermediate risk for breast cancer progression, in particular where the primary tumour of the patient has been graded as Nottingham grade 2 (NHG2).

It is very surprising that NHG2 tumors can be clearly classified into two groups, in a way that can not be done even by established biomarkers such as Ki67 (See FIGS. 13-14).

In one embodiment the cancer progression risk determination is carried out using a digital image of the same sample that was used for the previous determination of the progression risk for the patient.

In one embodiment the trained neural network has been validated after step b) using a dataset comprising the clinical outcome for a plurality of patients, where each of the patients has previously presented histology samples which had been assigned one histology grade score selected from the three histology grade scores.

In a second aspect of the invention there is provided a system comprising progression risk module configured to determine a cancer progression risk for a breast cancer patient by receiving a digital image of a histological sample from the patient and providing the digital image to trained neural network, the progression risk module being further configured to produce a cancer progression risk determination based on the image, where the neural network has been trained by a) receiving a training dataset comprising digital images of histology samples from breast cancer patients where each histology sample is associated in the dataset with one histology grade score selected from a set comprising three histology grade scores: a first histology grade score indicating low risk for progression of the cancer disease, a second histology grade score indicating intermediate risk for progression of the cancer disease and a third histology grade score indicating high risk for progression of the cancer disease, b) using the digital images of histology samples associated with the first and third histology grade scores, while ignoring digital images associated with the second histology grade score, to train the neural network for determining the cancer progression risk for a patient.

The system may comprise an image processing module configured to divide a received digital image into a plurality of sub areas and storing each sub area as a separate digital image, where the progression risk score module is configured to allow the trained neural network to determine a cancer progression risk for each of the plurality of images, resulting in a plurality of cancer progression risk values, and further configured to determine a global cancer progression risk by using the plurality of risk values.

There is also provided a method for training a neural network comprising the steps:

a) providing a training dataset comprising digital images of histology samples from cancer patients where each histology sample is associated in the dataset with one histology grade score selected from a set comprising three histology grade scores: a first histology grade score indicating low risk for progression of the cancer disease, a second histology grade score indicating intermediate risk for progression of the cancer disease and a third histology grade score indicating high risk for progression of the cancer disease, b) using the digital images of histology samples associated with the first and third histology grade scores, indicating low risk and high risk, respectively, while ignoring digital images associated with the second histology grade score indicating intermediate risk, to train a neural network for determining the cancer progression risk for a patient.

DRAWINGS

The accompanying drawings form a part of the specification and schematically illustrate preferred embodiments of the invention, and serve to illustrate the principles of the invention.

Figures 5, 6:
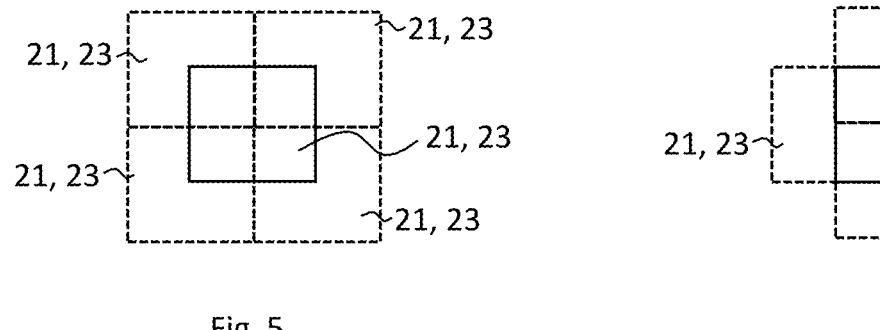

FIGS. 5 and 6. schematically show overlap.

Figures 7, 8, 9:
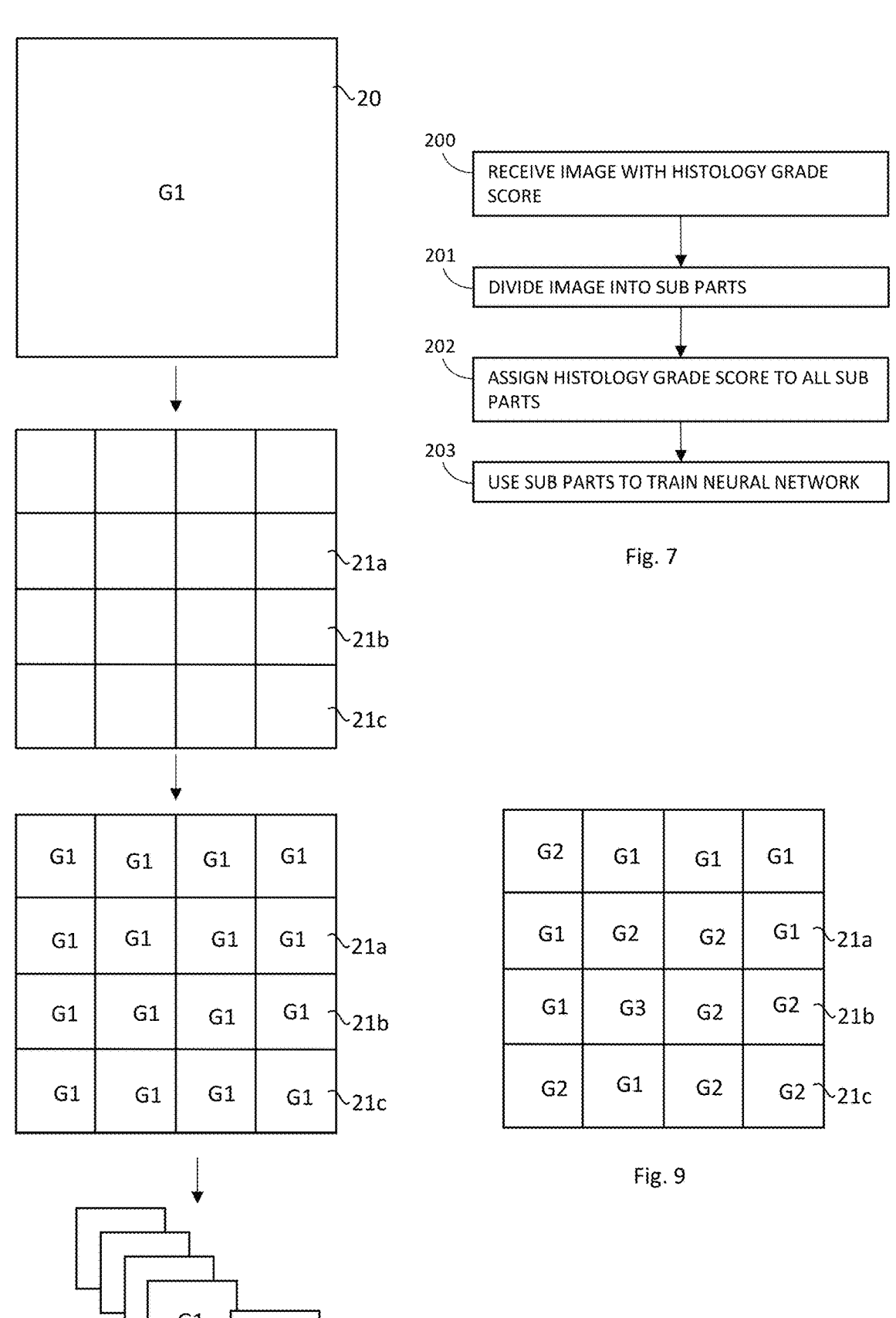

FIG. 7 is a flowchart showing a method.

FIG. 8 schematically show tiling in relation to a training dataset.

FIG. 9 shows tiles as hypothetically graded by a pathologist.

Figure 10:
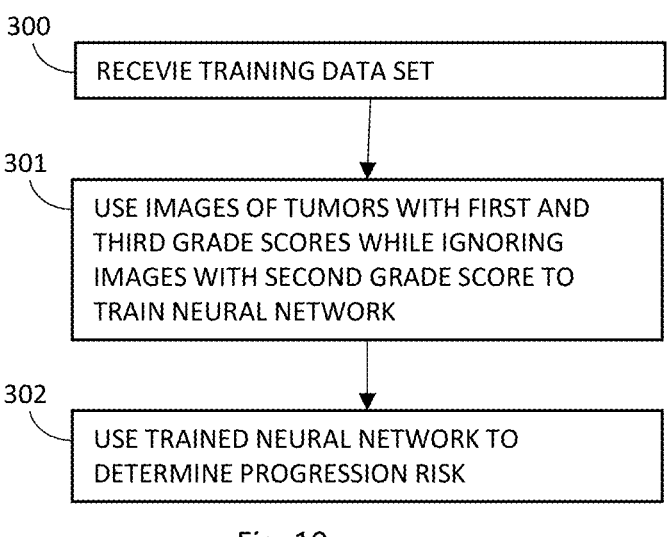

FIG. 10 is a flowchart showing a method.

Figures 11, 12:
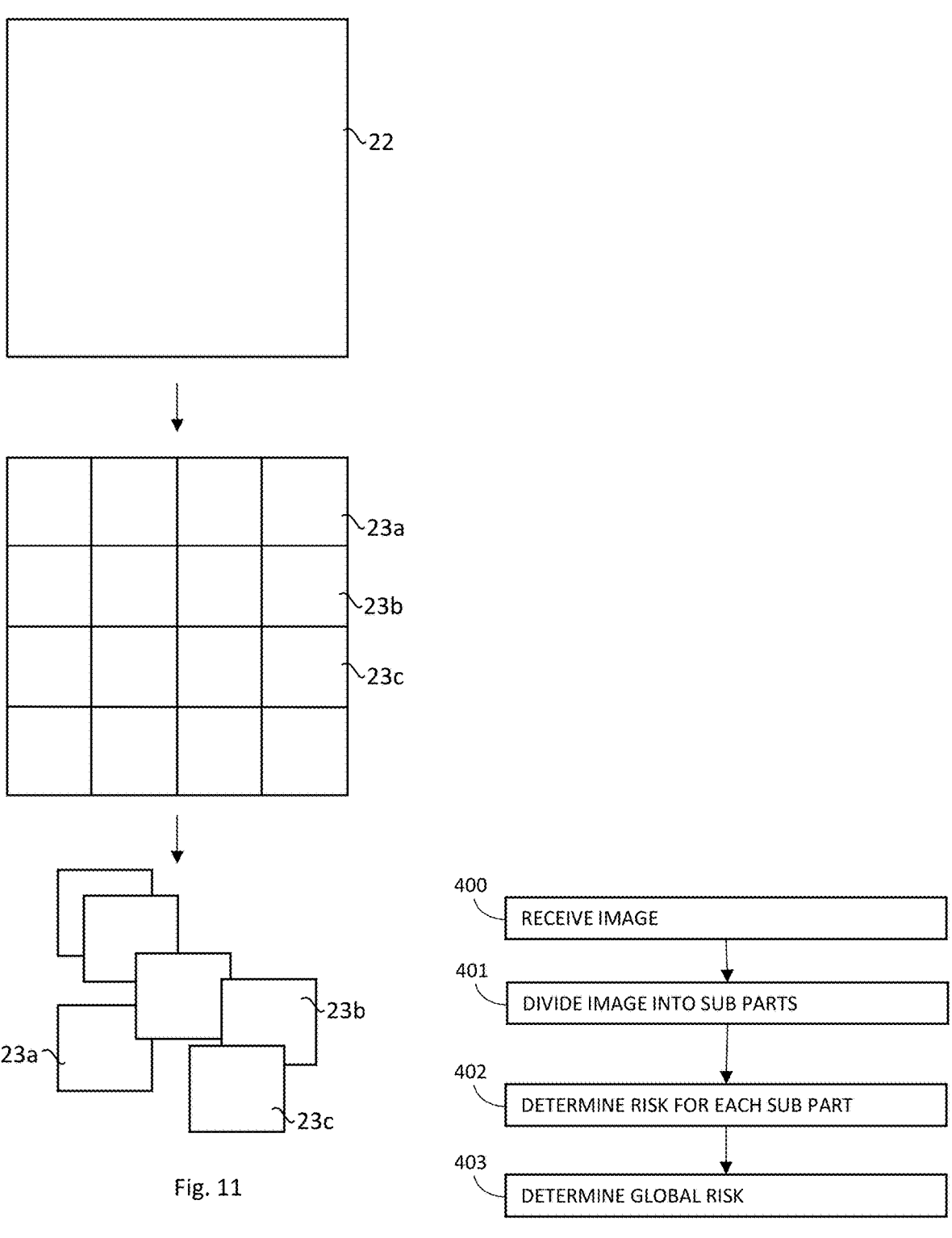

FIG. 11 schematically show tiling in relation to risk determination.

FIG. 12 is a flowchart showing a method.

Figure 13:
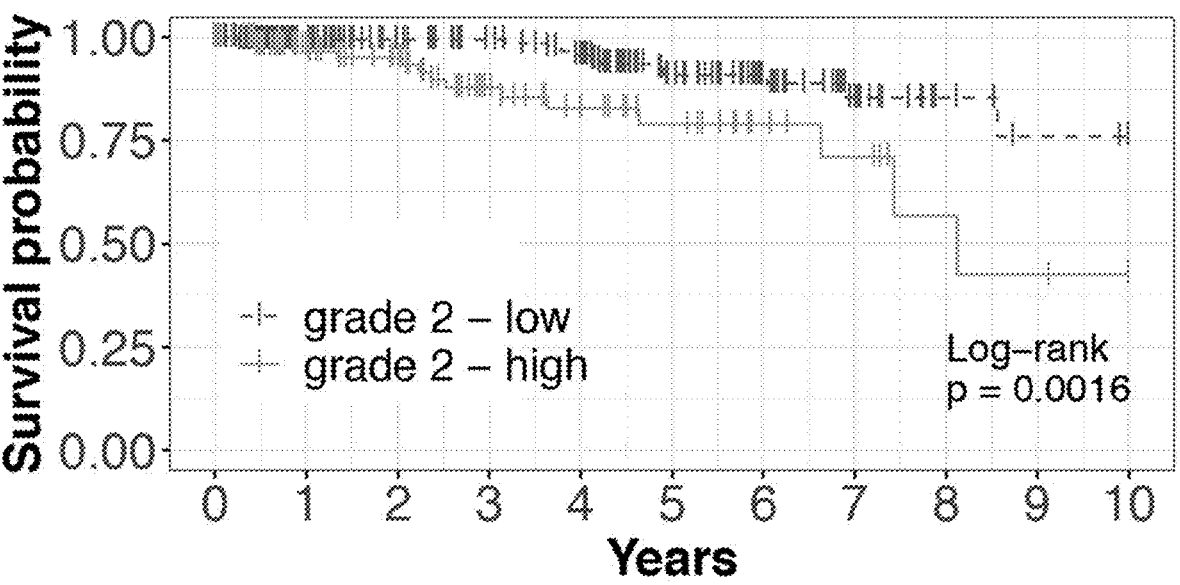

FIG. 13 shows recurrence-free survival outcomes for grade NHG2 breast cancer patients stratified by the Experimental Model displayed as a Kaplan-Meier curves, confirming distinct difference in patient outcomes in the grade 2-low and high groups.

Figure 14:
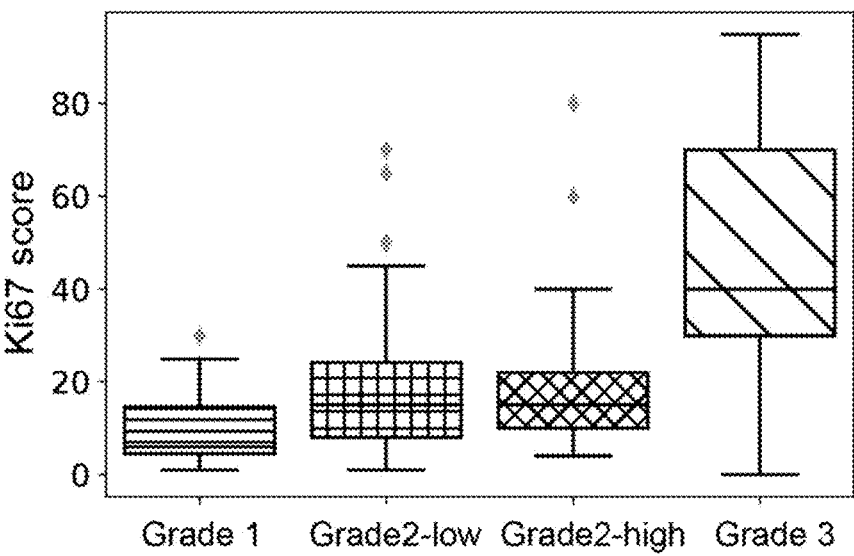

FIG. 14 shows Distribution of Ki67 score between NHG 1, NHG 2 (split into low and high risk group by the Experimental Model), and NHG 3. The plot shows that there is no significant different between the Grade2-low and high groups, confirming that Ki67 cannot be used as an alternative to the Experimental Model.

Figure 15:
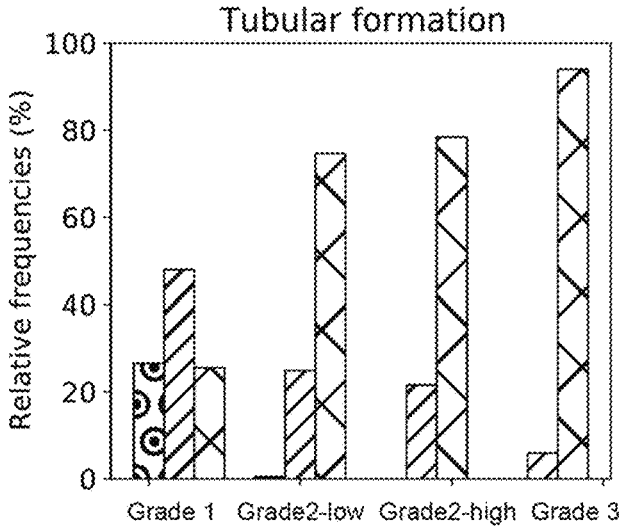
Figure 15:
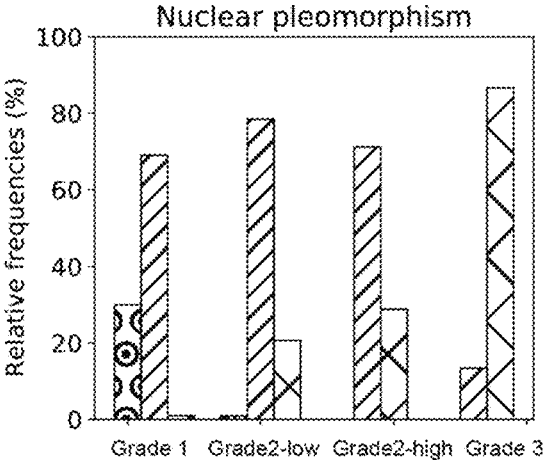
Figure 15:
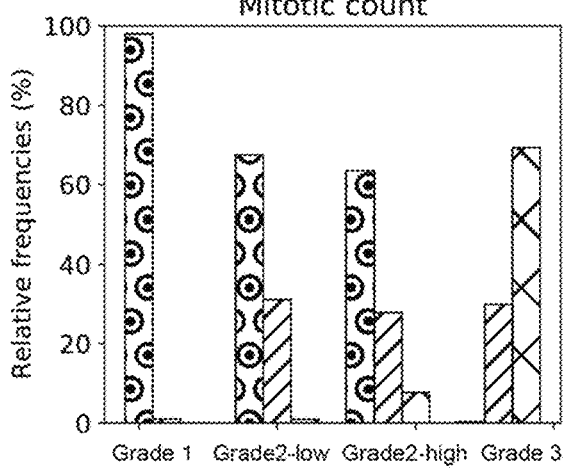
Figure 15:
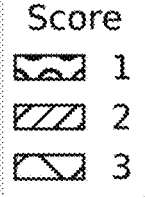

FIG. 15 shows distribution of the three histological grade subcomponent scores (mitotic count, nuclear polymorphism and tubular formation) for NHG 1, NHG 2 (split into low and high-risk group by the Experimental Model), and NHG 3, confirming that that these measures cannot be used as an alternative to the Experimental Model.

DETAILED DESCRIPTION

In this disclosure, histological grading is discussed. In histological grading of breast cancer typically three histology grade are typically used: a first histology grade (G1) score indicating low risk for progression of the cancer disease, a second histology grade (G2) score indicating intermediate risk for progression of the cancer disease and a third histology grade score (G3) indicating high risk for progression of the cancer disease. The first histology grade score may be a NHG1 (Nottingham Histological grade 1) grade score, the second grade score may be a NHG 2 grade score and the third grade score may be a NHG 3 grade score. In other embodiments the Elston and Ellis histological grade or the Scarff-Bloom-Richardson grading score, or any derivatives of these systems may be used. The histology grade score may relate to a part of a primary tumor that has been removed during surgery, or to a biopsy from the primary tumour obtained as a pre-operative biopsy.

"Risk for cancer progression" or "cancer progression risk" can be expressed by any type of risk parameter such as, for example, classifying a patient as belonging to a certain risk group, such as a histological grading groups, or the patient having a tumour that is similar to such a group, an uncalibrated cancer progression risk score, or any other type of risk for cancer progression. A risk score may be a value between 0 and 1, or a numerical value in any range.

The cancer progression risk score may be an uncalibrated numerical metric for the tumor of the patient to progress. In particular "risk for cancer progression" may be an uncalibrated risk score expressed as a value between 0 and 1, or a numerical value in any range, indicating how similar a sample, or an image of a sample, is to a certain histological grade score such as a NHG grade score such as for example NHG3.

The risk score, in particular when the patient has previously been graded as having an intermediate risk for progression, can, in one embodiment, be provided as one of two classes: more similar to having a low risk for progression (grade 1-similar) or more similar to having a high risk (grade 3-similar).

A histological sample from a biopsy is produced by methods well known in the art of pathology. A biopsy of a tumour is preferably from a region of the body that has cancer or suspected of having cancer. The biopsy is preferably taken from a patient that previously has been diagnosed with cancer. The tumour is preferably a primary tumour. The biopsy has been removed from the body of the patient. The methods described herein are not performed on the body of the patient, as the biopsy has already been removed from the patient.

In breast cancer, the biopsy is often isolated in connection with surgical removal of the primary tumour. Tissue that includes the tumor is then saved for later analysis. A biopsy may also have been removed using core needle biopsy.

The biopsy is prepared by chemical treatment (for example by fixation using formaldehyde) and embedding in a second material, for example in paraffin. Typically, the material is then sliced into thin slices or tissue sections (with a thickness of for example from 3 μm to 10 μm more preferably from 4 μm to 5 μm) using for example a microtome. The sample is preferably stained so that morphology of the tissue is enhanced. Useful stains include haematoxylin and eosin staining. One or more sections are then selected and mounted on glass slides, for example glass slides that are suitable for microscopy. The stained and mounted tissue section is referred to as a "sample" or a "histological sample" herein.

Figure 1:
FIGS. 1 to 2 are schematic drawings of software components of a system.

With reference to FIG. 1, system 1 may before and during training comprise training dataset 2, neural network 3 architecture, and an imaging processing module 4. Examples of useful neural network architectures include deep convolutional neural networks (for example, Inception V3 or V4, ResNet18 or 50, VGG, Xception, RexNext50) or other deep neural networks for image recognition. System 1 may also comprise image selection software 15 arranged to select images associated with data (such as metadata or data in a database) indicating a certain histology grade scores, and provide them to the neural network for training. Image selection software 15 may in particular be arranged to prevent images associated with an intermediate risk grade score to be provided to the neural network for training. Image selection software 15 may for example be arranged as a logical filter. The logical filter may exclude images associated with data indicating an intermediate risk. Image selection software 15 may comprise a set of pre-defined rules.

The training dataset 3 preferably comprises images from a large number of patients, where each image is from one patient. Preferably one patient has contributed at most one image from one tumour to the training dataset 3. The number of images (before tiling) is preferably at least 500, more preferably at least 10,000. The training dataset 2 may be arranged in any suitable manner, for example as a database or as image files together with data table. In the training dataset 2, each original image is associated with a previously assigned histology grade. The histology grade has been determined by a pathologist as known in the art of pathology.

For example, in a table there is a pointer to each image file and to a histological grade. An schematic and hypothetical table is shown in Table 1.

TABLE 1

| Patient | Link to image | Histology Grade |
|---------|---------------|-----------------|
| 1 | abc | NHG 3 |
| 2 | bcd | NHG 1 |
| 3 | cde | NHG 1 |
| 4 | def | NHG 2 |
| 5 | efg | NHG 3 |
| N | xxx | xxx |

When the images have been tiled, they are associated with a histological grade as described above. The training dataset 2 may be referred to as the "ground truth".

Figure 2:
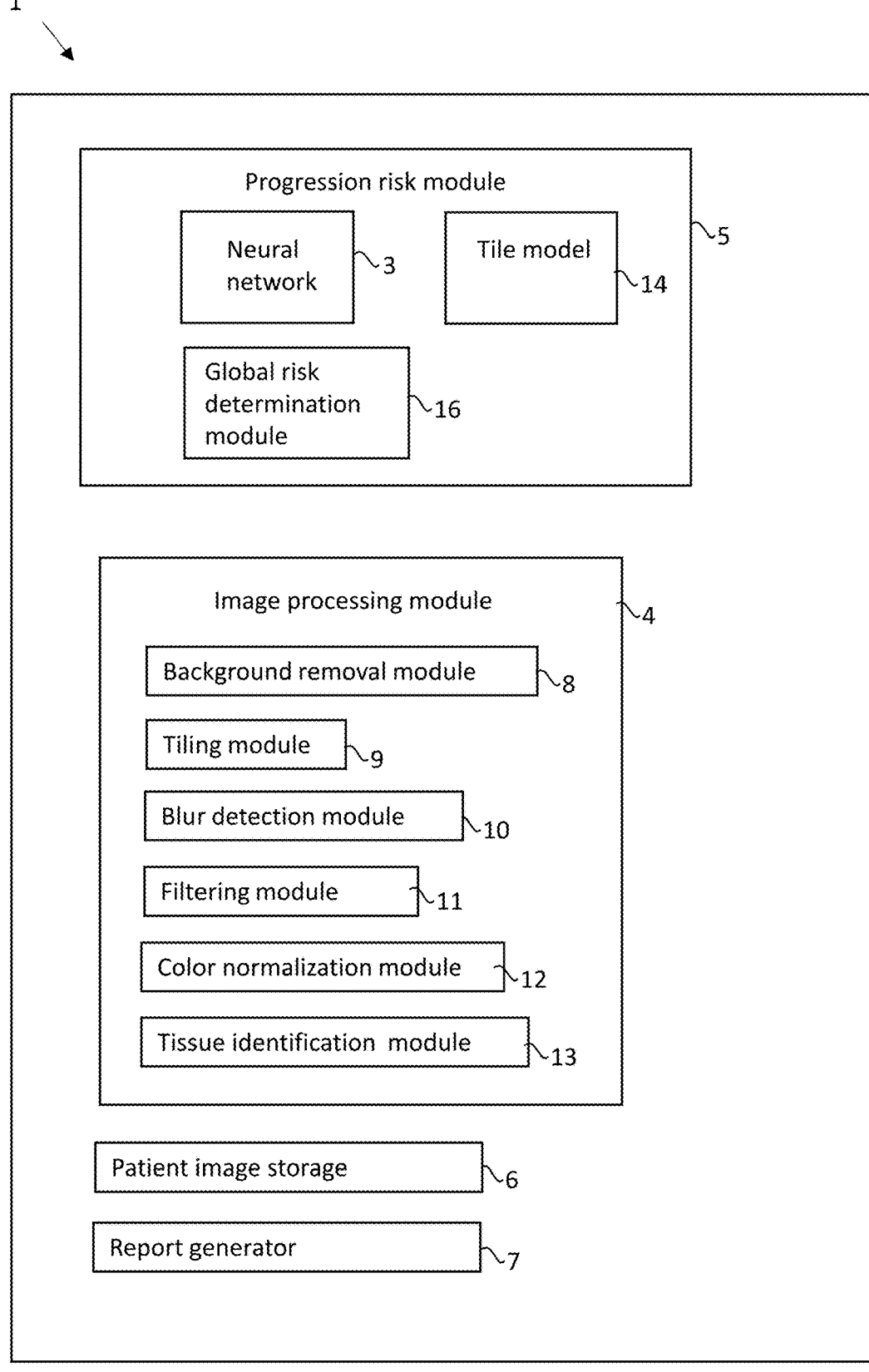

When the neural network 3 has been trained, system 1 can be used to determine a cancer progression risk for a patient, and the system 1 does not need to comprise the training dataset 2 (FIG. 2). System 1 may then comprise a progression risk module 5 comprising the trained neural network 3, and imaging processing module 4. Progression risk module 5 may also comprise software, such as for example a global risk determination module 16, for using risk values for a plurality of tiles to determine a global risk for the patient, for example by averaging, as described below with reference to FIG. 12. System 1 may also comprise patient image storage 6 for storing digital images of samples to be analyzed by progression risk module 5 and a report generator 7 for generating a report to a user, for example a pathologist. The progression risk module 5 may provide data to the report generator 7 for generation a report to the user. The report generator may provide a report in any suitable form such as .html or .pdf. The report may comprise information about cancer progression risk for an individual patient.

Image processing module 4 may comprise one or more of the following parts which are described in more detail below: background removal module 8, tiling module 9, blur detection module 10, filtering module 11, color normalization module 12 and tissue identification module 13.

Figure 3:
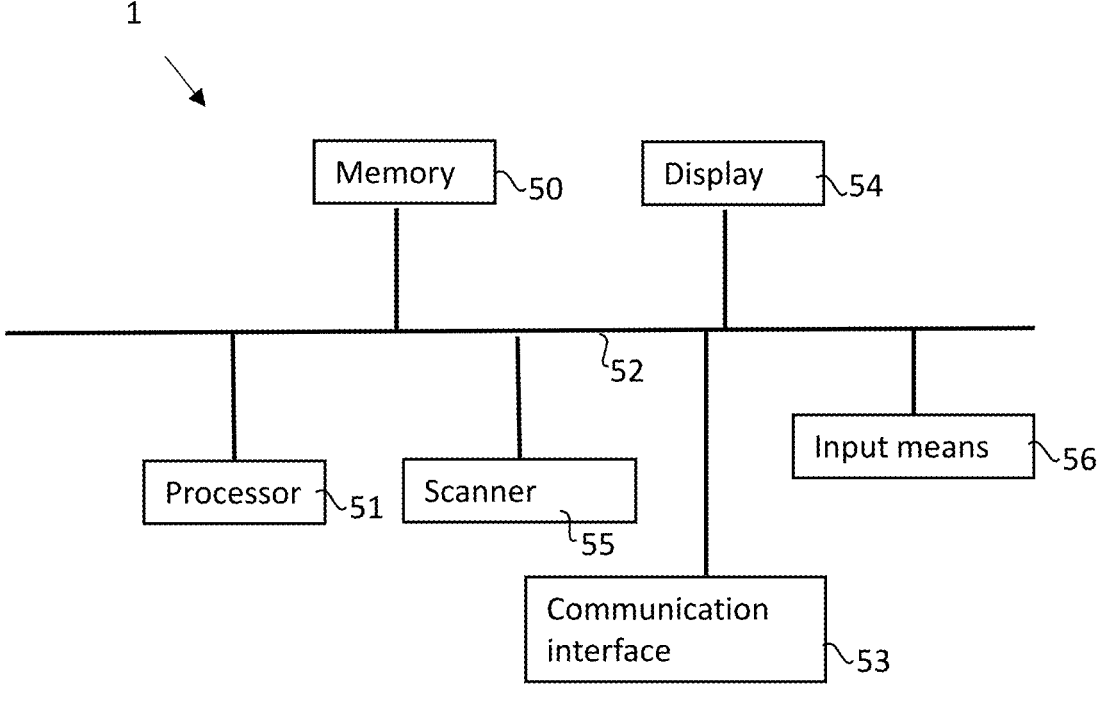
FIG. 3 is a schematic drawing of hardware components of a system.

FIG. 3 shows various hardware components of system 1 including memory 50, processor 51, bus 52, communication interface 53, display 54, scanner 55 and input means 56 (for example a mouse, keyboard or touch screen).

Digital images of the histological samples are produced using conventional means. The samples may be scanned using a digital pathology slide scanner 55. Digital images may be captured with the use of a microscope or other arrangement that magnifies the sample in a suitable way.

In general, digital images are processed as follows. A digital image in a suitable format is produced for example by scanner 55. The image typically represents a two-dimensional surface of the sample. The image may represent a field of view from for example a microscope. The digital image is preferably represented as a number of pixels arranged in a matrix pattern (bitmap image). Suitable formats include .jpg and .tiff but also proprietary file formats may be used. The pixel size (width of pixel) may represent from about 0.1μ to 2 μm of the sample. The image is preferably a colour image.

Figure 4:
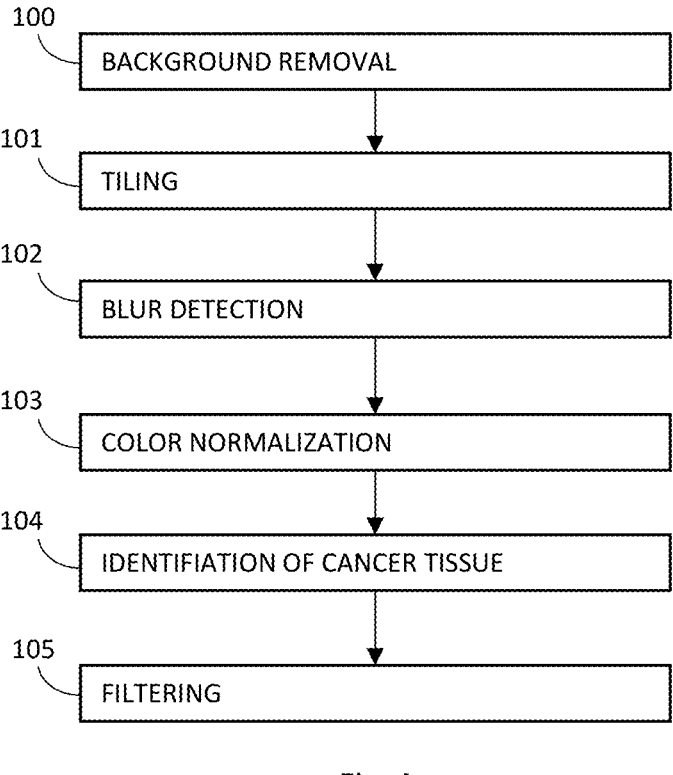
FIG. 4 is a flowchart showing a method.

The image may then be pre-processed. Pre-processing may include one or more steps such as background removal, tiling, blur detection, filtering, colour normalization, and cancer tissue identification. The steps may be carried out in any suitable order for example the order shown in FIG. 4. Methods that describe various useful pre-processing steps are described in Wang Y, Kartasalo K, Weitz P, Acs B, Valkonen M, Larsson C, Ruusuvuori P, Hartman J, Rantalainen M. Predicting molecular phenotypes from histopathology images: a transcriptome-wide expression-morphology analysis in breast cancer. Cancer Research. 2021 Jan. 1.

Pre-processing may include removal of background (non-tissue parts of image), step 100. This is done by background removal module 8.

The images are preferably divided into sub-areas ("tiles") by tiling module 9 (tiling, step 101). This has the advantage of improving processing by the system 1. The sub areas are preferably square. The subareas preferably have equal size. The sub areas are preferably arranged in a matrix pattern (FIGS. 5, 6, 8 and 11). Initially one image may represent a tissue sample with a size of about 1 mm-3 cm in diameter. One image can suitably be divided into from 10 to 100 000 sub areas (tiles), or more preferably from 16 (4×4 tiles) to 99856 (316×316 tiles). The size of each tile is preferably from 100×100 pixels to 5000×5000 pixels, more preferably from 500×500 pixels to 4000×4000 pixels. Each tile preferably consists of the same number of pixels. The size of the tile may be selected depending on the model and computational hardware used. The size of the tile may be selected by a user. Suitable software packages for carrying out the tiling and which may be included in the tiling module 9 includes Python, NumPy and OpenCV.

When tiles are used, the tiles may be overlapping, such that some or all areas are present in more than one tile. Preferably the tiles do not share at least one edge. The overlap may be from 10-90% of the area of a tile. An advantage with overlapping the tiles is that features close to the edges of a tile are assessed more accurately by the neural network. When the tiles are square it is preferred that overlap is in both the X and Y direction in the image plane. FIG. 5 shows an example of overlap where each tile 21, 23, is overlapped by four other tiles 21, 23 where each overlapping tile (dashed) covers 25% of the area of the first tile (solid line). FIG. 6 shows an image where each tile is overlapped by four tiles, where each tile covers 50% of the area of the first tile.

The tiles 21, 23 may be saved as image files in the system 1 (in training dataset 2, when the original image is part of dataset 2 or saved in patient image storage 6 when the original image is used for cancer progression risk determination). The file may be saved in the same way as the original image. The same file format or a different file format may be used.

Blur detection may be carried out by blur detection module 10 in step 102 to remove parts of images that are not in focus.

Pre-processing may also include colour normalization, step 103, to account for variably in staining procedures across laboratories and also scanners used. This is done by colour normalization module 12.

An image typically comprises both healthy tissue and cancer tissue. In subsequent step 104, the cancer tissue in the image is identified. Parts of the image that do not represent cancer tissue is excluded. Hence such parts may be excluded from further processing. This can be done in different manners. In one embodiment a pathologist has identified which pixels in the image that are cancerous, or which are healthy, or both. This information may for example be associated with the image file as metadata. The metadata may identify pixels or parts of the image that are cancerous or healthy. System 1 uses the information to exclude healthy tissue. Alternatively, identification is done by the system 1 itself for example by using machine learning, for example as described in Wang Y et al cited above. This step is carried out by tissue identification module 13.

Next, the images in the dataset may be filtered in step 105 by filtering module 11. For example, small areas in the image that represent healthy tissue embedded in an area of invasive cancer may be filtered away. A single tile (when tiles are used) may be filtered away. Also, small cancer areas embedded by surrounding healthy tissue may be removed. A threshold, for example a threshold for the number of pixels may be used. The threshold may be for example between from 300 pixels to 1000 pixels. Areas that are below the threshold may be excluded from downstream process steps.

Again, steps 100-105 may be carried out in any suitable order. Filtering step 105 is preferably carried out after tissue identification step 104. Blur detection step 102 and color normalization step 103 is preferably carried out before tissue identification step 104.

In a preferred embodiment, when tiling of images in training dataset 2 is used, each tile from the original image in the training dataset 2 is associated, in the training dataset, with the histology grade score of the original image. The original image may comprise tissue parts that would have been assigned different grades by a pathologist, for example if a pathologist graded each tile separately. This information is not used in this embodiment but each tile is instead assigned the histology grade score of the original image.

With reference to FIG. 7, a method may comprise the steps of step 200, receiving an digital image 20 from the dataset 2, (where each digital image is associated with data representing a histology grade score) step 201 dividing the digital image 20 associated with the histology grade score in the training dataset into a plurality of image sub areas (tiles) 21 and storing each image sub area as a separate digital image, step 202 assigning, in the training dataset 2, the histology grade score associated with the initial image 20 to every digital image of a sub area 21, and step 203 using some or all images of the sub areas 21 as classified in step 202 to train the neural network 3. The images of the sub-parts 21 may be stored in the training dataset 2. FIG. 8 shows an example of an initial image 20 which is graded as indicating a low risk of cancer progression (G1). When the image 20 is divided into tiles 21a, 21b, 21c, and all tiles are assigned the same grade (low risk=G1). Information about the grade score is stored associated with the tile in the training dataset 2. Hence the same grading is applied to all tiles 21 regardless of how they would actually be scored by a pathologist. Hence, at least two sub areas 21 of at least one image may depict tissue that would have been graded differently from each other by a pathologist only looking at that sub image. FIG. 9 shows an example of how a pathologist would have graded each of the sub parts 21 in the exemplary image 20. Subpart 21a and 21b are assigned different grades (low risk grade, G1, for 21a and intermediate risk grade, G2, for 21b) by a pathologist. However, in the dataset 2, subparts 21a and 21b both have a grading of low risk (G1) because the initial grading of the initial image 20 is low risk (G1). The tiling and saving of images of sub parts is carried out by tiling module 9. Tiling module 9 may also assign a grade score to each sub image and store associate data representing a grade score with each sub image, for example in the image database.

When the images have been pre-processed, they (or the tiles) can be used in machine learning. Training of the neural network 3 may be done as follows. With reference to FIG. 10, in step 300, the training dataset 2 comprising the images (preferably as tiles as described above) and the histology scores are provided to neural network 3 in order to train it. The neural network 3 may be any type of useful neural network such as a deep neural network or a convoluted neural network. Other types of machine learning may also be used. Machine learning and neural network as such are known and described elsewhere, see for example Goodfellow, Ian, Yoshua Bengio, and Aaron Courville. Deep learning. MIT press, 2016; Russell, Stuart, and Peter Norvig. "Artificial intelligence: a modern approach." (2002); Friedman, Jerome H. The elements of statistical learning: Data mining, inference, and prediction, Springer open, 2017. Start values for gradient decent may be provided to the neural network 3 by a user, but may also be generated randomly by a module in the system 1.

In step 301, the neural network 3 is trained. The neural network is preferably trained to identify the grade score of the sample in the image. The neural network may be trained to recognize how similar an image is to a histology grade score, for example using a grade score class probability. Hence, the neural network may be trained to recognize how similar an image is to images of a certain histology grade score. The neural network may be trained to provide this as cancer progression risk as described above, for example as an uncalibrated risk score.

The neural network 3 is preferably trained using only histology samples indicating a low risk for cancer progression (for example NHG 1) and histology samples indicating a high risk for cancer progression (for example NHG 3). Hence, in a preferred embodiment any images relating to a tumour with an intermediate cancer progression risk (for example NHG 2) in the training dataset 2 may be ignored. The exclusion of images with intermediate cancer progression risk may be carried out by suitable software for example image selection software 15. Table 2 shows the same table as Table 1 but after exclusion of intermediate risk patients, for example by filtering of data. Patient number 4 has been excluded.

TABLE 2

| Patient | Link to image | Histology Grade |
|---------|--------------|-----------------|
| 1 | abc | NHG 3 |
| 2 | bcd | NHG 1 |
| 3 | cde | NHG 1 |
| 5 | efg | NHG 3 |
| N | xxx | xxx |

In one embodiment the trained neural network 3 is validated or tuned using a separate dataset of images of histology samples from tumors from patients where the separate dataset comprises data about the clinical outcome for the patients, where the tumors of the patients has previously been assigned, by a pathologist, one histology grade score selected from the three histology grade scores.

In step 302, the trained neural network is used to predict the cancer progression risk for an individual patient. For risk determination, such as risk score determination, a digital image of a histological sample from the patient is provided to the trained neural network 3. A user (for example a pathologist) may store an image in patient image storage 6, for example by uploading the image from a remote location. The image is stored in a memory. The image is preferably stored associated with the identity of the patient in some manner. The image is preferably not present in the training dataset 2. The provided image may be pre-processed by image processing module 4 as described with reference to FIG. 4 (steps 100 to 105). The image is then provided to the trained neural network 3 and the trained neural network 3 then provides a cancer progression risk. The cancer progression risk may preferably be provided as a cancer progression risk score as described above.

It is noted that steps 300-302 are carried outside the body of any patient, as they are carried out using previously captured images of previously isolated samples from the patients.

The cancer progression risk determination is preferably carried out for a patient who has previously been considered to have an intermediate risk for breast cancer progression, for example having a NHG2 grade tumour. The patient may be a patient who has previously produced a sample from a tumour that has been graded by a pathologist as having at most an intermediate risk for progressing, such a NHG2 grade. The image provided to the neural network may be an image of the same sample that has been considered by the pathologist for grading the patient.

Tiling may be used when determining the progression risk for a cancer patient (Step 201). With reference to FIGS. 11 and 12, the image 22 provided to the system 1 is hence divided into sub area images (tiles) 23*a*, 23*b*, 23*c*. In step 400 the image is provided from the patient image storage 6 to the tiling module 9. In step 401 the image is divided by tiling module 9 into a plurality of image sub areas 23*a*, 23*b*, 23*c*. One or more tiles 23 may be used after filtering, etc. The tile images are stored in the patient image storage 6 associated with the identity of the patient. Tile images are stored using any suitable method or file format as described herein.

The progression risk is determined as a numerical value separately for each tile 23*a*, 23*b*, 23*c*. Hence, in step 402 a cancer progression risk value for each of the tiles 23*a*, 23*b*, 23*c* may be determined resulting in a plurality of cancer progression risk values. Each of the tile images are provided to the trained neural network 3. Hence for one single initial image 22 there will be plurality of numerical values. The risk values are stored in memory 50 associated with each tile 23*a*, 23*b*, 23*c*.

The cancer progression risk for the patient (global progression risk) may then be determined based on the plurality of numerical risk values. In step 403 a global progression risk is determined by the progression risk module 5 using the plurality of risk values, for example by a global risk determination module 16 in progression risk module 5 (FIG. 2). This can be done in different manners. This may be done for example by determining a summary statistics value for the plurality of risk values. Examples of useful summary statistics are: average risk score and the median risk score. As a theoretical example when an average is used, if the risk values for three tiles are 0.8, 0.6 and 0.4, the global progression risk will be the average of these values, which is 0.6. The number of risk values will typically be larger such as 16 or more. A different option is to use the n:th percentile, for example the $75^{th}$ percentile of the numerical risk values.

In a different embodiment a separate tile model 14 (statistical model, machine learning model, neural network, or similar) (which is different from the first neural network 3) which have been trained on cancer progression risk values assigned to tiles, is used for step 403. Preferably a different dataset has previously been used for training the tile model 14. The plurality of risk scores is provided to tile model 14 which then determines the global progression risk.

In one embodiment, a combination of using a summary statistics value for risk determination and trained tile model 14 is used. For example, a summary statistics value, such as the average of risk values, can be fed into a trained tile neural network 14 together with the plurality of risk values.

The invention has been described in relation to breast cancer. However, the risk of progression for any type of cancer can be assessed using the method and system described herein such as prostate cancer, lung cancer, colon cancer, rectal cancer, liver cancer, kidney cancer, cervix cancer, endometrial cancer, bladder cancer, melanoma or pancreatic cancer. The system 1 should be trained on images of samples of the same type of cancer that is diagnosed. The system can be used when the set of histology grade scores comprises other numbers than three scores such as two, four or five scores. An example of a five-score system is the Gleason scale which has five scores.

In general, a training dataset comprising digital images of histology samples from cancer patients where each histology sample is associated in the dataset with one histology grade score selected from a set comprising at least three histology grade scores: a first histology grade score indicating low risk for progression of the cancer disease, a second histology grade score indicating intermediate risk for progression of the cancer disease and a third histology grade score indicating high risk for progression of the cancer disease. Hence, one or more intermediate cancer risk group may be excluded from a training data set. In one embodiment only groups with the most extreme risks (the group with the highest risk and the group with the lowest risk) are included.

The excluded group preferably amount to at least 10% more preferably at least 20%, even more preferably at least 25%, even more preferably at least 40%, even more preferably at least 45%, and most preferably at least 50% of the number of patients in the original dataset. The rest of the patients are included in the dataset.

It is understood that the present methods and system is computer-implemented, using digital computer equipment. The various embodiments and components of system 1 described herein such as training dataset 2, neural network 3 and image processing module 4, progression risk module 5, patient image storage 6 and report generator 7, and communication between these components uses digital computer technology for storing and handling digital information and signals as well as suitable hardware and software, including for example suitable digital processors, digital memories, input means, output means, buses and communications interfaces. System 1 may have an operating system.

A user may be able to make input using input means 56 for example a keyboard, a mouse or a touch screen. Output, such as a report from report generator 7, may be provided on for example a display 54. A report may comprise a cancer progression risk for a patient.

The various parts of system 1 may be distributed across several physical entities such as memory units and processors. For example, training dataset 2 may be stored separately from rest of system 1.

The methods herein can be implemented with any suitable combination of software and hardware. Any suitable programming language may be used for the software units and methods described.

Data communication in system 1 may be implemented using suitable networking technologies and protocols. Data communication can be wireless, or wire bound. Information may be exchanged over a wide area net such as internet. Data communication in system 1 may be encrypted.

A user may be able to provide an image 22 remotely and receive a report from system 1 remotely. For example, a user may be able to use a client to upload an image file to a part of system 1 which is a server and the server may provide the cancer progression risk to the client, for example provided in a report.

It is realized that everything which has been described in connection to one embodiment is fully applicable to other embodiments, as compatible. Hence, the invention is not limited to the described embodiments, but can be varied within the scope of the enclosed claims. While the invention has been described with reference to specific exemplary embodiments, the description is in general only intended to illustrate the inventive concept and should not be taken as limiting the scope of the invention. The invention is generally defined by the claims.

EXAMPLE

Method

Routine histopathology whole sample (slide) images stained with hematoxylin and eosin (HE) from 1,567 breast cancer patients were used for model optimization, validation and testing. The test set consisted of 372 histological grade 2 (NHG2) cases out of the 1,567 included breast cancer cases. The main outcome was recurrence free survival.

Digital whole slide images were tiled into tiles of 598× 598 pixels with a down sampled resolution equivalent to 20× (271×271 μm). Unsharp tiles were excluded. Colour normalization was applied to adjust for stain and image colour variation. Only tissue areas that were manually annotated as invasive cancer, or predicted as invasive cancer by a cancer detection model, were included in subsequent analyses. Image pre-processing methods have been described in detail previously (Wang, Yinxi, et al. "Predicting molecular phenotypes from histopathology images: a transcriptome-wide expression-morphology analysis in breast cancer." Cancer Research (2021).

An ensemble of 20 base CNN models with the Inception V3 model architecture (Szegedy, Christian, et al. "Rethinking the inception architecture for computer vision." Proceedings of the IEEE conference on computer vision and pattern recognition. 2016), with model weights initialized from a model pre-trained with the ImageNet dataset (Russakovsky, Olga, et al. "Imagenet large scale visual recognition challenge." International journal of computer vision 115.3 (2015): 211-252) was optimized for binary classification of histological grade 1 and grade 3 cases (NHG1 and NHG3). The CNN models were trained on tile-level data using a weakly supervised approach where all tiles from each tumour were assigned with the tumour-level histological grade label. Models were optimized using stochastic gradient descent to obtain a trained network (the "Experimental Model". The ensemble model was subsequently applied to the histological grade 2 (NHG2) cases in the test set to dichotomize them into grade 2-high and grade 2-low groups. Ensemble predictions were averaged at the tile-level. The 75th percentile of the tile-level predictions for each slide was used as the slide level prediction. The decision threshold for dichotomization of grade 2 cases was estimated as the optimal decision boundary between histological grade 1 and 3 images, using Youden's method (Youden, William J. "Index for rating diagnostic tests." Cancer 3.1 (1950): 32-35). Prognostic performance of the model in the stratification of histological grade 2 cases was evaluated using Kaplan-Meier curves and Cox Proportional Hazard model analysis, with recurrence free survival as outcome, adjusting for established clinical risk-factors (age, tumor size, estrogen receptor status, lymph node status, human epidermal growth factor receptor 2 status). Furthermore, assessment of differences in the distribution of the proliferation marker Ki67 (as determined by Immunohistochemistry) and the distribution of histological grade subcomponents were performed.

Data analyses were performed using Python (v 3.6), including scikit-image modules (v 1.13.1), OpenCV (v 3.4.1), OpenSlide (v.3.4.1 and API v. 1.1.1). Deep learning models were optimized using Keras [v 2.2.4, with Tensorflow (v 1.12) backend].

Results

The model provides independent prognostic information when applied to histological grade 2 cases to dichotomize them into a high and a low risk group (FIG. 13—Kaplan Meier plot), with estimated Hazard Ratio (Cox Proportional Hazards model)=2.94 (95% CI=1.24-6.97, P=0.015) for grade 2-high compared with the grade 2-low risk group. There was no significant difference in Ki67 score between the grade 2-high and grade 2-low groups (P=0.625, Mann-Whitney U-test; FIG. 14—Ki67). Furthermore, comparing histological grade subcomponent scores (mitotic count, tubular formation, nuclear pleomorphism) between grade 2-high and grade 2-low groups (FIG. 15—subcomponent scores), there was no significant difference for tubular formation nor nuclear pleomorphism, while there was a small, but statistically significant difference for mitotic count (P=6.54×10-3, Fisher's exact test). The subcomponent score sum did not provide independent prognostic performance (Cox Proportional Hazards model, HR=1.19, 95% CI=0.46-3.10, P=0.715) indicating that the histological grade subcomponents do not contribute independent prognostic information.

The invention claimed is:

1. A computer implemented method for determining a cancer progression risk for a cancer patient, the method using a computer system comprising a processor and a memory with software stored thereon, the method comprising:

training a neural network by:

a) receiving a training dataset comprising at least 500 digital images of histology samples from cancer patients, the histology samples being stained to enhance morphology of the tissue, the digital images showing the morphology-enhancing stain, where each histology sample is associated in the dataset with one histology grade score selected from a set comprising three histology grade scores: a first histology grade score indicating low risk for progression of the cancer disease, a second histology grade score indicating intermediate risk for progression of the cancer disease and a third histology grade score indicating high risk for progression of the cancer disease, wherein each patient has contributed at most one image from one tumor to the training dataset, further comprising, for each digital image in the training dataset:

I. dividing the digital image into at least ten image sub areas of equal size and storing each image sub area as a separate digital image, and II. assigning, to each digital image representing an image sub area, the histology grade score of the digital image, b) selecting, using digital image selection software, from the plurality of digital images of sub areas of histology samples from step a) II that are associated with the first and third histology grade scores, the digital images of sub areas indicating low risk and high risk, respectively, while ignoring digital images associated with the second histology grade score indicating intermediate risk, to train a neural network for determining the cancer progression risk for a patient;

providing, from a patient image storage to the trained neural network, a digital image of a histological sample from a patient, the histological sample being stained to enhance morphology of the tissue, the digital image showing the morphology-enhancing stain; and determining, by the trained neural network, a cancer progression risk for the patient based on the provided digital image.

2. The method of claim 1 where at least two sub areas of at least one digital image depict tissue that would have been graded differently from each other by a pathologist looking only at that sub area of the digital image.

3. The method of claim 1 where cancer progression risk for the patient is determined by A. dividing the provided digital image of the histology sample from the patient into a plurality of image sub areas, B. determine cancer progression risk for each of the sub areas, resulting in a plurality of cancer progression risk values, C. determining a global cancer progression risk by using the plurality of risk values.

4. The method of claim 1 where the cancer progression risk score determination is carried out for a patient who has previously been considered to have a primary tumor which has been graded as Nottingham grade 2 (NHG2).

5. The method of claim 3 where the digital image of a histology sample from the patient is a digital image of a histology sample of a primary tumor of the patient which has been graded as Nottingham grade 2 (NHG2).

6. The method of claim 4 where the cancer progression risk determination is carried out using a digital image of the same histology sample that was used for the previous determination of the progression risk for the patient.

7. The method of claim 1 where the trained neural network has been validated after step b) using a dataset comprising the clinical outcome for a plurality of patients, where each of the patients has previously presented histology samples which had been assigned one histology grade score selected from the three histology grade scores.

8. The method of claim 1 where the cancer is breast cancer.

9. The method of claim 1 where the neural network has been trained to recognize how similar a digital image is to digital images of a certain histology grade score.

10. A computer system comprising a processor and a memory with software stored thereon and a progression risk software module stored in the memory, the progression risk software module comprising a trained neural network and being configured to determine a cancer progression risk for a cancer patient, wherein the neural network has been trained by:

a) receiving a training dataset comprising at least 500 digital images of histology samples from cancer patients, the histological samples being stained to enhance morphology of the tissue, the digital images showing the morphology-enhancing stain, where each histology sample is associated in the dataset with one histology grade score selected from a set comprising three histology grade scores: a first histology grade score indicating low risk for progression of the cancer disease, a second histology grade score indicating intermediate risk for progression of the cancer disease and a third histology grade score indicating high risk for progression of the cancer disease, wherein each patient has contributed at most one image from one tumor to the training dataset, further comprising, for each digital image in the training dataset:

I. dividing the digital image into at least ten image sub areas of equal size and storing each image sub area as a separate digital image, and II. assigning, to each digital image representing an image sub area, the histology grade score of the digital image, b) selecting, using digital image selection software, from the plurality of digital images of sub areas of histology samples from step a) II that are associated with the first and third histology grade scores, the digital images representing image sub areas indicating low risk and high risk, respectively, while ignoring digital images associated with the second histology grade score indicating intermediate risk, to train a neural network for determining the cancer progression risk for a patient;

wherein the progression risk software module is further configured to:

receive, from a patient image storage comprised in the memory of the system, a digital image of a histological sample from the patient, the histological sample being stained to enhance morphology of the tissue, the digital image showing the morphology-enhancing stain; and use the trained neural network to determine a cancer progression risk for the patient based on the provided image.

11. The system of claim 10, further comprising an image processing software module configured to divide a received digital image into a plurality of sub areas and storing each sub area as a separate digital image, wherein the progression risk software module further comprises a global risk determination software module configured to allow the trained neural network to determine a cancer progression risk for each of the plurality of digital images, resulting in a plurality of cancer progression risk values, and wherein the global risk determination software module is further configured to determine a global cancer progression risk by using the plurality of risk values.

12. The system of claim 10 wherein the cancer is breast cancer.

\* \* \* \* \*